US009547012B2

(12) United States Patent
Goldknopf (10) Patent No.: US 9,547,012 B2
(45) Date of Patent: Jan. 17, 2017

(54) DIAGNOSIS OF PARKINSON'S DISEASE

(75) Inventor: Ira Leonard Goldknopf, The Woodlands, TX (US)

(73) Assignee: Amarantus Bioscience Holdings, Inc., San Francisco, CA (US)

( * ) Notice: Subject to any disclaimer, the term of this patent is extended or adjusted under 35 U.S.C. 154(b) by 448 days.

(21) Appl. No.: 12/802,630

(22) Filed: Jun. 10, 2010

(65) Prior Publication Data
US 2010/0314251 A1 Dec. 16, 2010

Related U.S. Application Data

(60) Provisional application No. 61/268,235, filed on Jun. 10, 2009.

(51) Int. Cl.
*G01N 33/559* (2006.01)
*G01N 33/68* (2006.01)

(52) U.S. Cl.
CPC ... *G01N 33/6896* (2013.01); *G01N 2800/2821* (2013.01)

(58) Field of Classification Search
None
See application file for complete search history.

(56) References Cited

PUBLICATIONS

Sheta et al.; 2D gel blood serum biomarkers reveal differential clinical proteomics of the neurodegenerative diseases, Expert Rev. Proteomics 3(1), (2006), pp. 45-62.*
Abdi, et al. Detection of biomarkers with a multiplex quantitative proteomic platform in cerebrospinal fluid of patients with neurodegenerative disorders, J. Alzheimer's Dis. 9 (2006) 293-348.
Anderson, et al. High resolution two-dimensional electrophoresis of human plasma proteins, Proc. Nat. Acad. Sci. USA 74, (1977) 5421-5425.
Baba, et al. Alterations of T-lymphocyte populations in Parkinson disease. Parkinsonism Relat. Disord. 11 (2005) 493-8.
Bennett, et al. Prevalence of parkinsonian signs and associated mortality in a community population of older people, N. Engl. J. Med. 334 (1996) 71-76.
Bernheimer, et al. Brain dopamine and the syndromes of Parkinson and Huntington. Clinical, morphological and neurochemical correlations, J. Neurol. Sci. 20 (1973) 415-55.
Bezard, et al. Compensatory mechanisms in experimental and human parkinsonism: towards a dynamic approach, Prog. Neurobiol. 55 (1998) 93-116.
Bezard, et al. Structures outside the basal ganglia may compensate for dopamine loss in the presymptomatic stages of Parkinson's disease, FASEB J. 15 (2001) 1092-4.
Blalock, et al. Incipient Alzheimer's disease: microarray correlation analyses reveal major transcriptional and tumor suppressor responses, Proc. Natl. Acad. Sci. USA. 101 (2004) 2173-8.
Blandini, et al. Modifications of apoptosis-related protein levels in lymphocytes of patients with Parkinson's disease. The effect of dopaminergic treatment, J. Neural. Transm. 111 (2004) 1017-30.
Blandini, et al. Peripheral proteasome and caspase activity in Parkinson disease and Alzheimer disease, Neurology 66 (2006) 529-34.
Bonifati, et al. DJ-1(PARK7), a novel gene for autosomal recessive, early onset parkinsonism, Neurol. Sci. 24 (2003) 159-60.
Borovecki, et al. Genome-wide expression profiling of human blood reveals biomarkers for Huntington's disease, Proc. Natl. Acad. Sci. USA 102 (2005) 11023-8.
Braak, et al. Gastric alpha-synuclein immunoreactive inclusions in Meissner's and Auerbach's plexuses in cases staged for Parkinson's disease-related brain pathology, Neurosci. Lett. 396, (2006) 67-72.
Campion, et al. The NACP/synuclein gene: chromosomal assignment and screening for alterations in Alzheimer disease, Genomics 26 (1995) 254-7.
Schrag, et al. How valid is the clinical diagnosis of Parkinson's disease in the community? J. Neurol. Neurosurg. Psychiatry 73 (2002) 529-34.
Di Fonzo, et al. FBXO7 mutations cause autosomal recessive, early-onset parkinsonian-pyramidal syndrome, Neurology. 72 (2009) 240-5.
Dorsey, et al. Biomarkers in Parkinson's disease, Expert Rev. Neurother. 6 (2006) 823-31.
Emilsson, et al. Alzheimer's disease: mRNA expression profiles of multiple patients show alterations of genes involved with calcium signaling, Neurobiol. Dis. 21 (2006) 618-25.
Goldknopf, Blood-based proteomics for personalized medicine: examples from neurodegenerative disease. Expert Rev. Proteomics 5,1-8 (2008).
Goldknopf, et al. Complement C3c and related protein biomarkers in amyotrophic lateral sclerosis and Parkinson's disease. Biochemical and Biophysical Research Communications 342 (2006) 1034-1039.
Goldknopf, et al. Isolation and characterization of protein A24, a "histone-like" non-histone chromosomal protein, J. Biol. Chem. 250, (1975) 7182-7187.
Goldknopf, et al. Isopeptide linkage between nonhistone and histone 2A polypeptides of chromosomal conjugate-protein A24, Proc. Nat. Acad. Sci. USA 74, (1977) 864-868.
Goldknopf, et al. Presence of protein A24 in rat liver nucleosomes, Proc. Nat. Acad. Sci. USA 74, (1977) 5492-5495.
Goldknopf, et al. Remarkable similarities of peptide fingerprints of histone 2A and nonhistone chromosomal protein A24, Biochem. Biophys. Res. Commun. 65, (1975) 951-960.
Goldknopf, Molecular diagnostics and proteomics on the outskirts of personalized medicine, Joint Meeting of the Molecular Diagnostics and Cancer Proteomics World Congresses, Expert Rev. Mol. Diagnostics 7, (2007) 339-343.
Greenamyre, et al. Biomedicine. Parkinson's—divergent causes, convergent mechanisms, Science. 304 (2004) 1120-2.

(Continued)

*Primary Examiner* — Antonio Galisteo Gonzalez
(74) *Attorney, Agent, or Firm* — Wilson Sonsini Goodrich & Rosati (57) ABSTRACT

A method of diagnosing Parkinson's disease uses the abnormal concentrations of a group of 21 blood serum protein biomarkers. The concentration of the 21 protein biomarkers is assessed in a patient's serum by quantitative two-dimensional polyacrylamide gel electrophoresis.

16 Claims, 3 Drawing Sheets

(56) References Cited

PUBLICATIONS

Hedrich, et al. Distribution, type, and origin of Parkin mutations: review and case studies, Mov. Disord. 19 (2004) 1146-57.

Sheta, et al. 2D gel blood serum protein biomarkers reveal differential clinical proteomics of the neurodegenerative diseases. Expert Rev. Proteomics 3(1), (2006) 45-62.

Hoehn, et al. Parkinsonism: onset, progression, and mortality, Neurology 17 (1967) 427-42.

Jankovic, et al. Parkinson Study Group, The evolution of diagnosis in early Parkinson disease, Arch. Neurol. 57 (2000) 369-72.

Kalman, et al. Gene expression profile analysis of lymphocytes from Alzheimer's patients, Psychiatr. Genet. 15 (2005) 1-6.

Kitada, et al. Mutations in the parkin gene cause autosomal recessive juvenile parkinsonism. Nature. 392 (1998) 605-8.

Klose, Protein mapping by combined isoelectric focusing and electrophoresis of mouse tissues. A novel approach to testing for induced point mutations in mammals, Humangenetik. 26, (1975) 231-243.

Kruger, et al. Ala30Pro mutation in the gene encoding alpha-synuclein in Parkinson's disease, Nat. Genet. 18 (1998) 106-8.

Kruger, et al. LRRK2 in Parkinson's disease—drawing the curtain of penetrance: a commentary. BMC Med. 6 (2008) 33.

Kuerer, et al. Identification of distinct protein expression patterns in bilateral matched pair breast ductal fluid specimens from women with unilateral invasive breast carcinoma. Cancer 95, (2002) 2276-2282.

Kuncewicz, et al. Proteomic analysis of S-nitrosylated proteins in mesangial cells. Mol. Cell. Proteomics 2, (2003) 156-163.

Lang, et al. Parkinson's disease, Review, First and Second of two parts, N. Engl. J. Med. 339, (1998) 1130-53.

Langston, The Parkinson's complex: parkinsonism is just the tip of the iceberg. Ann. Neurol. 59 (2006) 591-6.

Leroy, et al. The ubiquitin pathway in Parkinson's disease, Nature 395 (1998) 451-2.

Lopez, et al. High-resolution serum proteomic profiling of Alzheimer disease samples reveals disease-specific, carrier-protein-bound mass signatures, Clin. Chem. 51 (2005) 1946-54.

Maes, et al. Transcriptional profiling of Alzheimer blood mononuclear cells by microarray, Neurobiol. Aging 28 (2007) 1795-809.

Margolis, et al. 2-dimensional resolution of plasma proteins by combination of polyacrylamide disc and gradient gel electrophoresis, Nature 221 (1969) 1056¬ 1057.

Markopoulou, et al. Candidate genes and Parkinson's disease: where to next? Neurology 53 (1999) 1382-3.

Michell, et al. Biomarkers and Parkinson's disease, Brain 127 (2004) 1693-705.

O'Farrell, et al. High resolution two-dimensional electrophoresis of proteins, J. Biol. Chem. 250, (1975) 4007-4021.

Olson, et al. The NH2- and COOH-terminal amino acid sequence of nuclear protein A24, J. Biol. Chem.251, (1976) 5901-5903.

Orrick, et al. Comparison of nucleolar proteins of normal rat liver and Novikoff hepatoma ascites cells by two-dimensional polyacrylamide gel electrophoresis, Proc. Nat. Acad. Sci. USA 70 (1973) 1316-1320.

Paisan-Ruiz, et al. Cloning of the gene containing mutations that cause PARK8-linked Parkinson's disease, Neuron. 44 (2004) 575-7.

Peng, et al. Alterations in Barrett's-related adenocarcinomas: A proteomic approach. Int. J. Cancer 122, (2008) 1303-1310.

Spillantini, et al. Alpha-synuclein in Lewy bodies, Nature 388 (1997) 839-40.

Polymeropoulos, et al. Mutation in the alpha-synuclein gene identified in families with Parkinson's disease. Science. 276 (1997) 2045-7.

Ricciarelli, et al. Microarray analysis in Alzheimer's disease and normal aging, IUBMB Life 56 (2004) 349-54.

Rodriguez, et al. How is firing activity of substantia nigra cells regulated? Relevance of pattern-code in the basal ganglia, Synapse. 49 (2003) 216-25.

Ross, et al. Genetic variation of Omi/HtrA2 and Parkinson's disease, Parkinsonism Relat. Disord. 14 (2008) 539-43.

Teunissen, et al. Combination of serum markers related to several mechanisms in Alzheimer's disease. Neurobiol. Aging 24 (2003) 893-902.

Tolosa, et al. The diagnosis of Parkinson's disease, Lancet Neurol. 5 (2006) 75-86.

Trojanowski, et al. Parkinson's disease and related synucleinopathies are a new class of nervous system amyloidoses, Neurotoxicology 23 (2002) 457-60.

Ueda, et al. Tissue-dependent alternative splicing of mRNA for NACP, the precursor of non-A beta component of Alzheimer's disease amyloid. Biochem. Biophys. Res. Commun. 205 (1994) 1366-72.

Valente, et al. Hereditary early-onset Parkinson's disease caused by mutations in PINK1. Science. 304 (2004) 1158-60.

Wolters, et al. Parkinson's disease: premotor clinico-pathological correlations, J. Neural. Transm. Suppl. 70 (2006) 309-19.

Zarranz, et al. The new mutation, E46K, of alpha-synuclein causes Parkinson and Lewy body dementia. Ann. Neurol. 55 (2004) 164-73.

Zimprich, et al. Mutations in LRRK2 cause autosomal-dominant parkinsonism with pleomorphic pathology, Neuron. 44 (2004) 601-7.

\* cited by examiner

DIAGNOSIS OF PARKINSON'S DISEASE

CROSS REFERENCE TO RELATED APPLICATIONS

The present application, pursuant to 35 U.S.C. 111(b), claims the benefit of the earlier filing date of provisional application Ser. No. 61/268,235 filed Jun. 10, 2009, and entitled "Diagnosis of Early Stage Parkinson's Disease: Abnormal Blood Serum Concentrations of a Select Group of Protein Biomarkers."

FIELD OF THE INVENTION

The present invention relates in general to a method for diagnosing Parkinson's disease. In particular, the present invention relates a set of biomarkers and their use in the diagnosis of Parkinson's disease in humans.

DESCRIPTION OF THE RELATED ART

Parkinson's disease is a progressive and degenerative neurological disorder involving the loss of dopaminergic neurons in the substantia nigra of the brain. The patient looses the ability to direct or control movement in a normal manner. Parkinson's disease (PD) is a common disease among individuals over the age of 50. About 50% of the individual report symptoms occurring prior to that age and are classified as having early-onset Parkinson's disease.

A variety of medications provide some relief from the symptoms, but no drug can stop the progression of the disease. In some cases, surgery is an appropriate treatment, but typically physical therapy and muscle strengthening exercises are recommended by the physician.

The following symptoms are considered the signs of Parkinson's disease: (1) rigidity, stiffness or inflexibility of limbs and joints; (2) bradykinesis (an abnormal slowness of movement) or akinesis (the absence of movement); (3) tremors (the involuntary, regular, rhythmic shaking of a limb, the head, the mouth, the tongue or the whole body); and (4) postural instability (an impaired balance or coordination).

Signs of Parkinsonism are often considered to be benign symptoms of aging. However, Parkinsonism is prevalent among people over the age of 65 in the general population. Studies show that 15% of people between the ages of 65-74 have Parkinsonism, and increasing age correlates with an increased percentage of Parkinsonism (i.e., 30% between the ages of 75-84, and over 50% in people age 85 and over) (1).

Parkinson's disease is difficult to diagnose and of the people in the general population with Parkinsonism only about 10% received a clinical diagnosis of Parkinson's disease (1). Yet the presence of Parkinsonism gives roughly a two fold increase in the risk of death (2).

There are a number of complication is diagnosing Parkinson's disease. One complication is that other conditions such as Alzheimer's disease (AD), sub-cortical vascular disease and multisystem atrophy can cause Parkinsonism (1). Furthermore, people with mild Parkinsonism often do not seek medical attention and if they do seek medical attention their physicians may not be able to accurately diagnose Parkinsonism or mild Parkinson's disease.

In general, by the time a person receives a diagnosis of Parkinson's disease, it is likely that substantial irreversible neurological damage has already occurred; rendering treatment less effective than if these people were brought to medical attention earlier. Physicians, clinicians, and patients would benefit greatly from a quick, early stage, and accurate diagnosis.

Multiple blood tests have been evaluated for PD diagnosis, including mitochondrial complex I, markers of oxidative stress, and dopamine metabolism (52-53), but these blood tests have not proven to be robust. The expression of individual genes has also been assessed in peripheral blood. Proteasome activity related to caspase-3 activation has been shown to be decreased in PD but not in AD patients (54-55). Molecular signatures of transcripts and protein levels in peripheral blood may serve as biomarkers for Huntington disease (56), AD, and amyotrophic lateral sclerosis (ALS) (22-25, 57-63). Proteomic profiling in AD CSF and blood by mass spectrometry of small peptides, derived from biomarker proteins by proteolysis, can discriminate between AD individuals and normal controls (54, 55, and 64), but provide limited information about the proteins and pathophysiological processes involved (21).

However, to date no blood test has been proven to be consistently reliable, specific and sensitive in the diagnosis of PD. Thus, despite the extensive information available regarding aspects of the pathogenesis of Parkinson's disease (PD) an accurate clinical diagnosis and staging of the disease remain challenging and misdiagnosis occurs in about 10 to 30% of patients, with early stages being especially prone to misdiagnosis (3-5).

Given the clinical and biochemical complexity of Parkinson's disease, the difficulty in its diagnosis and the inaccessibility of the brain to repeated sampling, there is a continuing need to identify a set of biomarkers to serve as indicators or sensors of the underlying biological process.

SUMMARY OF THE INVENTION

The present invention relates in general to a method for diagnosing Parkinson's disease. In particular, the present invention relates a set of biomarkers and their use in the diagnosis of Parkinson's disease in humans.

One embodiment of the invention is a method of diagnosing Parkinson's disease, the method comprising: collecting a serum sample from a test subject; analyzing the serum sample for a change in expression of a set of protein biomarkers; and using the change in expression of the set of biomarkers to diagnose the test subject.

Another embodiment of the invention is a set of biomarkers for diagnosing Parkinson's disease, wherein a change in the expression of the set of biomarkers in a serum sample of a test subject determines a positive or a negative diagnosis of Parkinson's disease in the test subject.

Yet another embodiment of the invention is a set of biomarkers comprising: Chain A Albumin mutant R218H protein, Haptoglobin HP-2a protein, Complement Factor I protein, Apolipoprotein E3 protein, Transthyretin dimer protein, Nucleoporin NUP 188 protein, Haptoglobin HP-1 protein, Albumin protein PRO2044, Parkinson's LB acidic H2A protein, Apolipoprotein A-IV protein, Transthyretin Huntington Interacting Protein E, Complement C4b gamma chain protein, Chain A Albumin mutant R218H protein, Fidgitin I protein, Immunoglobulin kappa light chain protein, Complement Factor H/Hs protein, Fidgitin II protein, Albumin protein PRO2675, and Haptoglobin related protein.

Still another embodiment of the invention is a method for diagnosing Parkinson's disease comprising: obtaining a serum sample from a test subject; electrophoresing a portion of the serum sample on a 2D gel, wherein the portion of the serum sample has a standardized protein concentration; determining a pixel cell density for each of at least twenty-one protein biomarkers in the 2D gel; and comparing the pixel cell density of each biomarker with a mean cell pixel density determined for control serum; whereby a variation in the pixel cell density of at least twenty-one biomarkers from a mean pixel cell density of the at least twenty-one biomarkers is a positive diagnosis of Parkinson's disease.

The foregoing has outlined rather broadly several aspects of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed might be readily utilized as a basis for modifying or redesigning the structures for carrying out the same purposes as the invention. It should be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Parkinson's disease (PD) is a progressive multisystem neurodegenerative disorder, an α-synucleinopathy, in which dopaminergic cell death exceeds a critical threshold [27, 28], and olfactory, autonomic, gastrointestinal dysfunction, dementia, depression, and sleep disorder sometimes appear prior to motor manifestations (29-30). PD has a long pre symptomatic phase where dopamine homeostasis compensates for dopaminergic neuronal loss. Breakdown of dopamine homeostasis results in alteration of basal ganglia output structures, and emergence of symptoms (31-32). PD is associated with multiple transmitter dysfunctions in dopamine, GABA, glutamate, acetylcholine, and enkephalin systems in the CNS (29, 33), in multiple brain regions, and peripheral tissues (34, 35). These findings provide support for the hypothesis that PD is not only a multi-neurotransmitter disorder but also a multi-system disorder.

The analysis of familial Parkinsonism has revealed that a wide spectrum of different types of gene mutations are associated with familial Parkinson's disease, including mutations in the α-synuclein (6-8, 36), parkin (37, 38), UCHL-1 (39)], DJ-1 (40), PINK1 (41, 42), LRKK2 (43, 44) Omi/Htra2 (45) and FBXO7 (46) genes. Differences in transcription and translation of non mutant forms of these genes, post-synthetic processing of their products, and additional molecular pathways, including mitochondrial function, protein turnover, oxidative stress, and inflammation, underlie similar manifestations of sporadic PD (47-51).

Despite the extensive information available regarding aspects of the disease pathogenesis, a consistently accurate method for the clinical diagnosis and staging of the disease is currently unavailable. For example, it has been reported that PD is misdiagnosed in about 10% to about 30% of patients, with the early stages of PD being particularly prone to misdiagnosis (3-5).

Given the complexity of PD, the difficulty in diagnosis and the inaccessibility of the nervous tissue, particularly the brain, to repeated sampling; the development of accessible biomarkers which can serve as indicators or sensors of the underlying pathophysiological processes is needed. From the extensive motor, cognitive, psychiatric, and autonomic symptoms, it is clear that multiple brain regions and peripheral tissues are affected in PD. Thus, the possibility that certain alterations in protein biomarkers can be used to diagnose PD was investigated.

The identification of biochemical markers from tissues, such as blood, that are easily accessible and accurately measured would represent a great advance in the diagnosis and treatment of PD. Since blood is the most accessible and routine physical source of biological material available for diagnostic testing, serum samples were mined for biomarkers for PD diagnostic development and testing.

Embodiments of the invention assessed the expression of numerous proteins found in serum as biomarkers for PD. This protein assessment was performed by two-dimensional polyacrylamide gel electrophoresis (2D gel electrophoresis).

2D gel electrophoresis has been used in research laboratories for biomarker discovery since the 1970's (9-18). In the past, this method has been considered highly specialized, labor intensive and non-reproducible to be applicable for diagnostic purposed. Only recently with the advent of integrated supplies, robotics, advances in software, as well as progress in data mining and bioinformatics has progression of this proteomic technique become feasible for consideration in diagnostics.

The promise and utility of 2D gel electrophoresis is based on its ability to detect changes in the expression of intact proteins and to separate and discriminate between specific intact protein isoforms that arise due to variations in amino acid sequence and/or post-synthetic protein modifications such as phosphorylation, ubiquitination, conjugation with ubiquitin-like proteins, acetylation, glycosylation, and proteolytic processing. These post-synthetic protein modifications and processes are critical features in cellular and physiological regulation, and are reflected by differentially expressed blood serum biomarkers in neurodegenerative diseases, including Alzheimer's and Parkinson's diseases, and ALS (24-25, 54-55).

Using a 2D gel electrophoresis proteomics platform (19-21), a combination of 59 specific biomarkers was found that distinguished the disease status in three neurodegenerative diseases: Alzheimer's disease (AD), Parkinson's disease (PD), and amyotrophic lateral sclerosis (ALS) (22-25) in retrospective stored samples from Houston, Tex., USA. A statistical model (i.e., a multivariate linear discriminant biostatistical analysis) was used to assess the concentrations of a set of protein biomarkers in the serum and to provide a probability score assigned to each blood sample that reflects the patient's disease status (23-25). This biomarker set was then assessed in a population of PD patients and age and ethnically matched controls from the region of Thessaly, Greece and cross validated with PD patients from Sun City, Ariz., USA.

Selection and Clinical Evaluation of Patient Subjects

Patients and age-matched controls were from three clinical sites: Baylor College of Medicine, Houston, Tex., USA (site 1); University of Thessaly, Larissa, Greece (site 2); and Banner Sun Health Research Institute, Sun City, Ariz., USA (site 3). The numbers of patients and controls for retrospective and prospective samples are listed in Table 1.

The study compared biomarker concentrations in serum samples of healthy participants and those with neurodegenerative diseases in the initial biomarker panel identification (site 1), and with PD in the extended investigation of the panel (sites 2 and 3).

All control subjects were healthy and had no family history of Parkinson's disease; while all PD subjects presented with at least three of the cardinal signs of idiopathic PD (i.e., resting tremor, bradykinesia, rigidity, postural instability, and response to levodopa or dopamine agonists).

TABLE 1

Patient and Control Samples

| Blood Serum Sample Type | Number of Patients | Disease Status |
|---|---|---|
| Retrospective Stored Samples[¥] | 115 | Alzheimer's disease (AD) |
| | 29 | Parkinson's disease (PD) |
| | 24 | AD/PD-like and Mixed[†] |
| | 75 | AD/PD Age-matched Normal Controls |
| | 136 | Amyotrophic lateral sclerosis (ALS) |
| | 33 | ALS-like[‡] |
| | 57 | ALS Age-matched Normal Controls |
| Prospective Newly Drawn Samples[§] | 62 | PD |
| | 78 | AD/PD Age-matched Normal Controls |

[†]AD/PD-like disorders including Frontotemporal dementia; Lewy body dementia; Vascular (Multi-infarct) dementia; Alcohol related dementia; Semantic dementia; Stroke (CVA); Post-irradiation Encephalopathy and Seizures; Vascular (Multi-infarct) parkinsonism; Multiple system atrophy; Essential tremor; Corticalbasal ganglionic degeneration; and mixed disorders including Alzheimer's disease combined with Vascular (Multi-Infarct) dementia; Alzheimer's disease combined with Lewy body dementia; Parkinson's disease combined with Lewy body dementia; Alzheimer's and Parkinson's disease combined with Lewy body dementia; Frontotemporal dementia combined with Chronic inflammatory demyelinating polyneuropathy; and Thalamic CVA combined with HX of Lung CA.
[‡]Non-ALS disorders of motor neurons, muscles, nerves, and spinal cord.
[¥]From Houston, TX, USA.
[§]From Thessaly, Greece and Sun City, AZ, USA Patients were excluded from the study if they exhibited: (1) causes of secondary Parkinsonism, including vascular Parkinsonism, encephalitis, exposure to neuroleptics, or the presence of additional signs such as dementia (MMSE<25), gaze palsy, amyotrophy, cerebellar signs, or symptomatic orthostatic hypotension (mean arterial pressure drop>20 mm Hg from recumbent to standing position); (2) an unstable medical condition; (3) a history of substance abuse; (4) major depression (Hamilton score>19); (5) a history of malignant melanoma; (6) an inability to understand the consent form; or (6) a history of drug or alcohol abuse.

The medical and demographic history of all subjects was evaluated, including the following patient information: (1) date of birth; (2) sex; (3) race; (4) date of blood sample collection; (5) rigidity; (6) bradykinesia/akinesia; (7) tremors; (8) postural instability; (9) history of past illness; (10) details of all current health problems; and (11) a copy of conventional images (CAT, PET scans, MRI of brain, SPECT, etc). All forms and copies of reports were identified by study number only in order to maintain confidentiality; a copy of the above mentioned medical information was sent to the testing site in accordance with Health Information Privacy concerns.

PD patients underwent clinical evaluation to provide clinical data, including the severity of PD symptoms, according to the Hoehn and Yahr Scale (2) and the Unified Parkinson's Disease Rating Scale (UPDRS) (26).

Sample Collection and 2D Gel Electrophoresis

Blood samples were collected from patients by venipuncture using standard red cap glass clot tubes without accelerator or gel. Serum samples were prepared from the blood by centrifugation after standing at room temperature for 30-45 minutes. The serum supernatant was collected, aliquoted, placed on dry ice, shipped to the laboratory, and stored at −80° C. until analyzed. Sample preparation and electrophoresis were performed essentially as described previously (19-22). The first dimension electrophoresis (100 µg of serum proteins/gel) was on immobilized 11 cm IEF strips (Bio-Rad Laboratories, Hercules Calif.), pH 5-8, and in the second dimension on pre-cast 8-16% acrylamide gradient CRITERION SDS-gels (Bio-Rad Laboratories, Hercules Calif.).

Fluorescent Staining and Digital Image Analysis and Normalization

The gels were stained (Lava Purple™, Fluorotechnics; SyproRuby™, Bio-Rad Laboratories, Hercules Calif.), fluorescent digital images captured (FLA 7000 Imager Fujifilm; FX Imager, Bio-Rad Laboratories), and protein spot detection and quantitation performed (PDQUEST™, Bio-Rad Laboratories, Hercules Calif.). Spot quantities in parts per million (PPM) fluorescent pixel spot density were normalized to total gel density.

Each serum sample was analyzed in duplicate or triplicate. Quantitation of individual spots was validated for linearity, dynamic range, limit of detection (LOD=0.66 µg/ml of serum), limit of quantify ability (LOQ=6.6 µg/ml of serum), reproducibility, and robustness (CV≤20%, Supplemental Material, FIG. 1A, B, Table 1).

Biostatistical Analysis

Initial control mean concentration values for 59 selected protein biomarkers were obtained. Age matched control samples (n=78) were subjected to multiple gel runs (n=178), and the quantitative protein analysis performed on 59 protein biomarkers of neurodegenerative disease. The results for each biomarker were subjected to individual biostatistical analysis using Analyse-it Software™ imbedded in Microsoft Excel. The results were compiled to yield a standard control mean value for each biomarker, which was then employed as a constant by which all the concentration values in the study were subsequently divided, to produce a Fold of Standard Normal Mean Concentration for each data point in the study.

Statistical significance of differences in individual biomarker blood serum concentrations (as Fold of Standard Normal Mean Concentration) between patient and controls was determined by non-parametric Dot Box and Whiskers (medians) and parametric Receiver Operator Characteristics analysis using Analyze-it Software™ in Microsoft XL. Analysis of joint performance of groups of biomarkers was by multivariate linear discriminant analysis using SAS® statistical software.

Box and Whisker plots give a visual representation of non-parametric descriptive statistics. The central "box" represents the distance between the first and third quartiles (inter quartile range or IQR), with the median marked as the horizontal line inside the box. The notch in the box represents the $95^{th}$% confidence interval around the median (the $50^{th}$ percentile); thus groups that display non-overlapping notches can be considered statistically different ($p<0.05$). The minimum value is the origin of the leading "whisker" and the maximum value is the limit of the trailing "whisker". All values are plotted individually (Dots) and those values outside the whiskers are considered possible outliers, presented either as circle (far outlier) or plus sign (near outliers).

The diagnostic performance of a test or the accuracy of a test to discriminate diseased cases from normal cases is evaluated using Receiver Operating Characteristic (ROC) curve analysis. ROC curves can also be used to compare the diagnostic performance of two or more laboratory or diagnostic tests. In a ROC curve the true positive rate (sensitivity) is plotted against the false positive rate (1-specificity) for different cut-off points. Each point on the ROC plot represents a sensitivity/specificity pair corresponding to a particular decision threshold. A test with perfect discrimination (no overlap in the two distributions) has a ROC plot that passes through the upper left corner (100% sensitivity, 100% specificity). Therefore the closer the ROC plot is to the upper left corner, the higher the overall accuracy of the test.

Multivariate discriminant analysis is a well-validated multivariate analysis procedure. Discriminant analysis identifies sets of linearly independent functions that will successfully classify individuals into a well-defined collection of groups. The statistical model assumes a multivariate normal distribution for the set of biomarkers identified from each disease group.

Discriminant analysis was applied to a training set of data, from which the contribution of each individual biomarker was determined. The step disk software program (SAS®) was then used to determine the linear combinations of biomarkers that provided an optimum classification of individuals into disease groups. Alternatively, the programmer manually selected different combinations of biomarkers to be incorporated into a linear or quadratic discriminant function to optimize the classification of individuals into disease groups.

The output of discriminant analysis (DA) is a classification table that permits the calculation of clinical sensitivity (how often the test is positive in diseased patients) and specificity (how often the test is negative in non-diseased individuals. Although a DA classification table also permits the calculation of the positive predictive value (PPV) and the negative predictive value (NPV), the PPV and NPV were not assessed in this study.

Selection of Specific Proteins Related to Neurodegenerative Disease in Retrospective Patient Samples Retrospective banked serum samples from patients with Alzheimer's disease (AD), PD, AD/PD-like and mixed disorders, amyotrophic lateral sclerosis (ALS), ALS-like and age-matched normal controls (Table 1) were analyzed by 2D gel electrophoresis, fluorescent staining, quantitative digital image analysis, and individual and multivariate biostatistics (22-25).

Fifty-nine protein biomarker spots were selected by exhaustive and painstaking comparisons of quantitative 2D gel images and individual protein concentration statistics (PPM pixel spot densities), which exhibited reproducible statistically significant abnormal, disease specific serum concentrations, differences between the following patient groups: AD vs. PD vs. ALS; AD vs. AD-like; PD vs. PD-like; ALS vs. ALS-like disorders; and familial vs. sporadic ALS. Multivariate discriminate analyses, in independent training and test sets, with combinations of sub-sets of the 59 biomarkers showed sensitivities and specificities of 85-95% (23-25).

Figure 1:
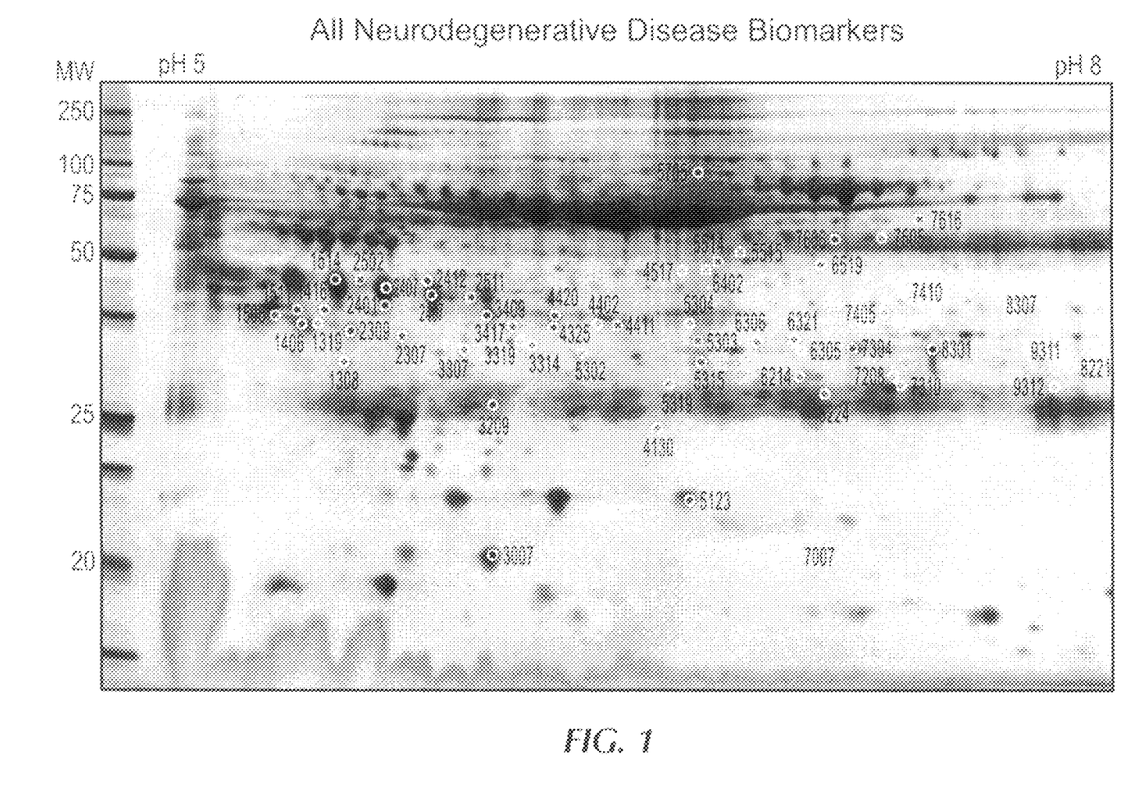
FIG. 1 is a digital fluorescent image of blood serum proteins resolved by 2-dimensional polyacrylamide gen electrophoresis. The 21 Step Disk Biomarkers are indicated by numbers and circles.

The proteins were characterized by in-gel trypsin digestion of protein spots, peptide LC MS/MS, spot molecular weights, isoelectric points, and Edman degradation where appropriate, to identify the protein molecular entities (see FIG. 1 and Table 2). The identified biomarker proteins clustered by function into four groups: I (cellular degeneration related); II (Haptoglobin proteins); III (inflammatory proteins); and IV (albumin proteins).

TABLE 2

Initial Set of Control Biomarkers

| No. | Spot No. | Accession No. | Protein Identity | Function |
|---|---|---|---|---|
| 1 | N5514 | 31615333 | Chain A Albumin mutant R218H protein | IV |
| 2 | N5123 | 4826762 | Haptoglobin HP protein | II |
| 3 | N5515 | | X1 | |
| 4 | N1416 | 4504579 | Complement Factor I | III |
| 5 | N3314 | 178849 | Apolipoprotein E3 | I |
| 6 | N3307 | 30483217 | Transthyretin "dimer" protein | I |
| 7 | N7007 | 55961147 | Nucleoporin NUP 188 | I |
| 8 | N2407 | 47124562 | Haptoglobin HP-1 Protein | II |
| 9 | N2511 | 6650826 | Albumin protein PRO2044 | IV |
| 10 | N6306 | 603553 | PDLaH Parkinson's LB acidic H2A protein (PADPR/Ub/A24) | I |
| 11 | N2502 | 37499461 | Apolipoprotein A-IV | I |
| 12 | N3007 | 48145933 37183102 | TTR; HYPE Huntingtin Interacting Protein E | I |
| 13 | N7304 | 1314244 | Complement C4b processing product C4 gamma Chain | III |
| 14 | N4420 | 31615333 | Chain A Albumin mutant R218H protein | IV |
| 15 | N8301 | 57997594 | Fidgitin I | I |
| 16 | N6224 | 2894829 | Immunoglobulin kappa light chain | III |
| 17 | N4411 | 2144888 | Complement Factor H/Hs protein | III |
| 18 | N6214 | 57997594 | Fidgitin II | I |
| 19 | N3417 | 7770217 | Albumin protein PRO2675 | IV |
| 20 | N4130 | | X2 | |
| 21 | N4402 | 67587 | Haptoglobin related protein | II |
| 22 | N5302 | 4557325 | Apolipoprotein E4 | I |
| 23 | N6402 | 177872 | Alpha-2-macroglobulin | I |
| 24 | N5705 | 14328065 | Aldehyde dehydrogenase 1 A3 | I |
| 25 | N7606 | 6573461 | Apolipoprotein H | I |
| 26 | N3209 | 337758 | Pre-serum Amyloid P protein | I |
| 27 | N2412 | 4102235 | AIM Apoptosis Inhibitor; CD5 Scavenger Receptor | I |
| 28 | N5304 | P46439 | Glutathione S Transferase Mu5-5 | I |
| 29 | N5303 | 52631746 | Lectin 3 P35 | I |
| 30 | N1308 | 223373 | Alpha-1-microglobulin | I |
| 31 | N1406 | 42716297 | Clusterin Isoform 1 | I |
| 32 | N3319 | 178851 | Preapolipoprotein E | I |
| 33 | N1514 | 47124562 | Haptoglobin HP-1 Protein | II |
| 34 | N2401 | 47124562 | Haptoglobin HP-1 Protein | II |
| 35 | N3409 | 47124562 | Haptoglobin HP-1 Protein | II |
| 36 | N2309 | 47124562 | Haptoglobin Protein | II |
| 37 | N5319 | 106529 | Immunoglobulin kappa C region protein | III |
| 38 | N6519 | 1335098 | Hemopexin | III |
| 39 | N7616 | 297569 | Complement Factor Bb protein | III |
| 40 | N7310 | 40786791 | Complement C3c1a | III |
| 41 | N7208 | 40786791 | Complement C3c1b | III |
| 42 | N7410 | 40786791 | Complement C3c1c | III |
| 43 | N9311 | 40786791 | Complement C3c2a | III |
| 44 | N9312 | 40786791 | Complement C3c2b | III |
| 45 | N1511 | 55648063 | Complement C3dg | III |
| 46 | N1506 | 180620 | Complement cytolysis inhibitor protein alpha subunit | III |
| 47 | N2307 | 1483187 | Inter α trypsin inhibitor heavy chain H4 related 35 KD protein | III |
| 48 | N4325 | 6650826 | Albumin protein PRO2044 | IV |
| 49 | N4517 | 31615333 | Albumin protein | IV |
| 50 | N5315 | 763431 | Similar to Albumin protein | IV |
| 51 | N7405 | 339469 | Transferrin protein | IV |
| 52 | N8307 | 339469 | Transferrin protein | IV |
| 53 | N5305 | | X3 | |
| 54 | N6414 | | X4 | |
| 55 | N6321 | | X5 | |
| 56 | N7320 | | X6 | |
| 57 | N1319 | | X7 | |
| 58 | N7505 | | X8 | |
| 59 | N8221 | | X9 | |

Verification of Clinical Usefulness in Prospective Freshly Drawn Samples from PD Patients A two site prospective clinical validation trial was conducted using freshly drawn samples from the University of Thessaly (56 PD patients, 30 age-matched normal controls) and Banner Sun Health Research Institute (6 PD patients and 48 age-matched normal controls). Age-matched control samples from the two sites (n=78) were subjected to duplicate or triplicate 2D gel runs (n=174, see Table 3).

TABLE 3

Combined Database of Control and PD Samples

|  |  | # of Gels | # of Patients |
|---|---|---|---|
| Control | Total | 174 | 78 |
| PD | Total | 165 | 62 |

Quantitative analysis performed on the 59 protein biomarkers followed by statistical analysis of individual biomarker proteins of this control group were used to calculate the standard normal control mean values for each biomarker (see Table 4). These were employed as constants by which all the spot PPM density values were divided to convert each data point from PPM spot density to Fold of Standard Normal Mean Concentration (FSN) for each biomarker.

TABLE 4

| Control N5302 > 0 | 17 Controls | 34 gels |
| Control N5302 = 0 | 61 Controls | 140 gels |

| Control for Normalization | Biomarker | n | Mean ± % SE |
|---|---|---|---|
| Control N5302 = 0 | N2307 | 140 | 15.8 ± 11.3% |
| Control N5302 = 0 | N3307 | 140 | 88.2 ± 10.1% |
| Control N5302 = 0 | N3314 | 140 | 200.9 ± 3.1% |
| Control N5302 = 0 | N4411 | 140 | 90.4 ± 10.5% |
| Control N5302 = 0 | N5123 | 140 | 1561.4 ± 8.5% |
| Control N5302 > 0 | N5302* | 34 | 72.6 ± 10.9% |
| Control N5302 = 0 | N5303 | 140 | 56.5 ± 3.4% |
| Control N5302 = 0 | N5304 | 140 | 81.6 ± 6.2% |
| Control N5302 = 0 | N6214 | 140 | 160.9 ± 3.3% |
| Control N5302 = 0 | N6224 | 140 | 101.7 ± 5.7% |
| Control N5302 = 0 | N6306 | 140 | 23.2 ± 4.5% |
| Control N5302 = 0 | N6321 | 140 | 35.4 ± 3.6% |
| Control N5302 = 0 | N6402 | 140 | 157.2 ± 6.7% |
| Control N5302 = 0 | N6519 | 140 | 90.5 ± 5.8% |
| Control N5302 = 0 | N7208 | 140 | 30.5 ± 8.8% |
| Control N5302 = 0 | N7304 | 140 | 155.8 ± 4.3% |
| Control N5302 = 0 | N7310 | 140 | 80.7 ± 8.8% |
| Control N5302 = 0 | N7405 | 140 | 101.2 ± 3.6% |
| Control N5302 = 0 | N7410 | 140 | 24.9 ± 5.8% |
| Control N5302 = 0 | N7616 | 140 | 67.9 ± 6.4% |
| Control N5302 = 0 | N8307 | 140 | 67.8 ± 5.2% |
| Control N5302 = 0 | N1308 | 140 | 350.6 ± 3.2% |
| Control N5302 = 0 | N1406 | 140 | 208.1 ± 2.4% |
| Control N5302 = 0 | N1416 | 140 | 123.0 ± 2.9% |
| Control N5302 = 0 | N1506 | 140 | 282.9 ± 3.7% |
| Control N5302 = 0 | N1511 | 140 | 11.7 ± 29.7% |
| Control N5302 = 0 | N1514 | 140 | 6971.0 ± 3.4% |
| Control N5302 = 0 | N2401 | 140 | 7664.1 ± 3.3% |
| Control N5302 = 0 | N2407 | 140 | 4403.3 ± 4.1% |
| Control N5302 = 0 | N2502 | 140 | 1134.2 ± 3.8% |
| Control N5302 = 0 | N2511 | 140 | 374.9 ± 4.2% |
| Control N5302 = 0 | N3209 | 140 | 643.4 ± 2.5% |
| Control N5302 = 0 | N3409 | 140 | 685.6 ± 3.6% |
| Control N5302 = 0 | N3417 | 140 | 230.6 ± 3.3% |
| Control N5302 = 0 | N4130 | 140 | 109.2 ± 2.4% |
| Control N5302 = 0 | N4325 | 140 | 369.3 ± 3.1% |
| Control N5302 = 0 | N4402 | 140 | 86.8 ± 9.3% |
| Control N5302 = 0 | N4420 | 140 | 391.8 ± 4.2% |
| Control N5302 = 0 | N4517 | 140 | 56.9 ± 13.0% |
| Control N5302 = 0 | N5315 | 140 | 402.4 ± 2.5% |
| Control N5302 = 0 | N5319 | 140 | 38.1 ± 4.7% |

TABLE 4-continued

| Control N5302 = 0 | N5514 | 140 | 376.4 ± 3.6% |
|---|---|---|---|
| Control N5302 = 0 | N7606 | 140 | 2279.9 ± 3.1% |
| Control N5302 = 0 | N9311 | 140 | 51.4 ± 6.0% |
| Control N5302 = 0 | N9312 | 140 | 63.1 ± 5.9% |
| Control N5302 = 0 | N1319 | 140 | 9.7 ± 31.6% |
| Control N5302 = 0 | N2309 | 140 | 200.2 ± 7.0% |
| Control N5302 = 0 | N2412 | 140 | 743.6 ± 4.5% |
| Control N5302 = 0 | N3007 | 140 | 2782.6 ± 2.6% |
| Control N5302 = 0 | N3319 | 140 | 2.0 ± 51.3% |
| Control N5302 = 0 | N5515 | 140 | 156.4 ± 8.7% |
| Control N5302 = 0 | N5705 | 140 | 527.8 ± 8.6% |
| Control N5302 = 0 | N6305 | 140 | 1.6 ± 29.6% |
| Control N5302 = 0 | N7007 | 140 | 347.7 ± 2.3% |
| Control N5302 = 0 | N7505 | 140 | 478.9 ± 8.0% |
| Control N5302 = 0 | N8221 | 140 | 8.1 ± 16.2% |
| Control N5302 = 0 | N8301 | 140 | 88.4 ± 4.4% |

| From | | Classified Into Diagnosis | | |
|---|---|---|---|---|
| Diagnosis | | PD | Control | Sensitivity | Specificity |
| PD | 15 | 15 | 0 | 100% | |
| PD | 31 | 28 | 3 | 90.3% | |
| PD | 46 | 43 | 3 | 93.5 | |
| Control | 30 | 2 | 28 | | 93.3% |

The serum concentration data (as FSN) of the 59 protein biomarkers were subjected to linear discriminant analysis (see Table 5A). A subgroup of the 59, namely 21 biomarkers, was selected by stepwise linear discriminant analysis, based on their complimentary contributions to the overall diagnostic classification of control vs. Parkinson's disease with the samples from Thessaly (Table 5B).

TABLE 5

Linear Discriminant Analysis of Patient and Control Data from Prospective Studies A. 57 Biomarkers

| | Classified into Diagnosis | | |
|---|---|---|---|
| From Diagnosis | Control Specificity | PD Sensitivity | Total |
| Control | 28 | 2 | 30 |
| | 93.3% | 6.7% | 100 |
| PD | 2 | 54 | 56 |
| | 3.6% | 96.4% | 100 |

B. 21 Biomarkers

| | Classified into Diagnosis | | |
|---|---|---|---|
| From Diagnosis | Control Specificity | PD Sensitivity | Total |
| Control | 28 | 2 | 30 |
| | 93.3% | 6.7% | 100 |
| PD | 4 | 52 | 56 |
| | 7.1% | 92.9% | 100 |

C. Additional Patients

| | Classified into Diagnosis | | |
|---|---|---|---|
| From Diagnosis | Control | PD Sensitivity | Total |
| PD | 0 | 6 | 6 |
| | 0% | 100% | 100 |

Additional Patients: Six serum samples from PD patients from the US correctly classified as PD obtained by the same discriminant function that was used in B, i.e., 21 biomarkers and trained by the database of patients and controls from Greece.

The linear discriminant function of each of the 21 selected biomarkers for the PD patients and the age-matched controls is given in Table 6.

TABLE 6

Linear Discriminant Function for Controls and Patients

| Variable | Linear Discriminant Function for PD | | Protein ID |
|---|---|---|---|
| | Control | PD | |
| Constant | −23.71 | −23.98 | |
| N5514 | 2.2395 | −0.725 | Chain A Albumin Mutant R218H Protein |
| N5123 | 1.2611 | 1.7463 | Haptoglobin HP-2a Protein |
| N5515 | 1.006 | 0.2698 | X1 Protein |
| N1416 | 3.877 | 7.0068 | Complement Factor I Protein |
| N3314 | 5.64 | 2.8679 | Apolipoprotein E3 Protein |
| N3307 | −0.07 | −1.395 | Transthyretin "Dimer" Protein |
| N7007 | 5.7858 | 7.9373 | Nucleoporin NUP188 Protein |
| N2407 | −0.692 | 0.4279 | Haptoglobin HP-1 Protein |
| N2511 | 3.5827 | 1.6327 | Albumin Protein PRO2044 |
| N6306 | 1.2861 | 0.0203 | PDLaH acidic H2A (ADPR/ub/A24) Protein |
| N2502 | 6.3247 | 4.6238 | Apolipoprotein A-IV Protein |
| N3007 | 3.3422 | 6.323 | Transthyretin HYPE Protein |
| N7304 | 2.2082 | 2.7762 | Complement C4b Gamma Chain Protein |
| N4420 | 1.3369 | 2.154 | Chain A Albumin mutant R218H Protein |

TABLE 6-continued

Linear Discriminant Function for Controls and Patients

| Variable | Linear Discriminant Function for PD | | Protein ID |
|---|---|---|---|
| | Control | PD | |
| N8301 | 4.7277 | 3.2318 | Fidgitin Protein I |
| N6224 | −0.191 | −1.053 | Immunoglobulin Kappa Light Chain Protein |
| N4411 | −0.259 | 0.0751 | Complement Factor H/Hs Protein |
| N6214 | 6.4806 | 7.6981 | Fidgitin Protein II |
| N3417 | 1.4272 | −0.253 | Albumin Protein PRO2675 Protein |
| N4130 | −2.076 | −0.61 | X2 Protein |
| N4402 | 0.1899 | 0.4446 | Haptoglobin Related Protein |

The 21 biomarkers selected by stepwise linear discriminant analysis as the optimal complimentary biomarker set contributing to the overall diagnostic classification of control vs. Parkinson's disease are identified as Nos. 1-21 in Table 2 and in Table 7B. When the resulting discriminant function was used (see Tables 6-8), 28 of 30 controls from Thessaly scored as controls (specificity=93.3%), and 52 of 56 PD patients from Thessaly scored as PD (sensitivity=92.9%). The six patients from Sun City that were not used in the generation of the discriminant function were all correctly classified.

TABLE 7

Summary Statistics for 21 Biomarkers

A: Summary Statistics:

| Step | Label | Partial R-Square | F Value | Pr > F | Wilks' Lambda | Pr < Lambda | Average Squared Canonical Correlation | Pr > ASCC | B: Biomarker protein Identities: | |
|---|---|---|---|---|---|---|---|---|---|---|
| | | | | | | | | | Biomarker | Protein ID |
| 1 | N5514 | 0.1019 | 26 | <.0001 | 0.8981 | <.0001 | 0.1019 | <.0001 | N5514 | Chain A Albumin Mutant R218H Protein |
| 2 | N5123 | 0.0594 | 14.39 | 0.0002 | 0.8447 | <.0001 | 0.1553 | <.0001 | N5123 | Haptoglobin HP-2a Protein |
| 3 | N5515 | 0.0592 | 14.3 | 0.0002 | 0.7947 | <.0001 | 0.2053 | <.0001 | N5515 | X1 Protein |
| 4 | N1416 | 0.0538 | 12.86 | 0.0004 | 0.7519 | <.0001 | 0.2481 | <.0001 | N1416 | Complement Factor I Protein |
| 5 | N3314 | 0.0432 | 10.16 | 0.0016 | 0.7194 | <.0001 | 0.2806 | <.0001 | N3314 | Apolipoprotein E3 Protein |
| 6 | N3307 | 0.0435 | 10.18 | 0.0016 | 0.6881 | <.0001 | 0.3119 | <.0001 | N3307 | Transthyretin "Dimer" Protein |
| 7 | N7007 | 0.0444 | 10.37 | 0.0015 | 0.6576 | <.0001 | 0.3424 | <.0001 | N7007 | Nucleoporin NUP188 Protein |
| 8 | N2407 | 0.0382 | 8.82 | 0.0033 | 0.6324 | <.0001 | 0.3676 | <.0001 | N2407 | Haptoglobin HP-1 Protein |
| 9 | N2511 | 0.052 | 12.13 | 0.0006 | 0.5995 | <.0001 | 0.4005 | <.0001 | N2511 | Albumin Protein PRO2044 |
| 10 | N6306 | 0.0316 | 7.18 | 0.0079 | 0.5806 | <.0001 | 0.4194 | <.0001 | N6306 | PDLaH acidic H2A (ADPR/ub/A24) Protein |
| 11 | N2502 | 0.0261 | 5.87 | 0.0163 | 0.5654 | <.0001 | 0.4346 | <.0001 | N2502 | Apolipoprotein A-IV Protein |
| 12 | N3007 | 0.0291 | 6.54 | 0.0113 | 0.549 | <.0001 | 0.451 | <.0001 | N3007 | Transthyretin HYPE Protein |
| 13 | N7304 | 0.0248 | 5.52 | 0.0196 | 0.5353 | <.0001 | 0.4647 | <.0001 | N7304 | Complement C4b Gamma Chain Protein |
| 14 | N4420 | 0.0233 | 5.14 | 0.0243 | 0.5229 | <.0001 | 0.4771 | <.0001 | N4420 | Chain A Albumin mutant R218H Protein |
| 15 | N8301 | 0.0179 | 3.93 | 0.0488 | 0.5135 | <.0001 | 0.4865 | <.0001 | N8301 | Fidgitin Protein I |
| 16 | N6224 | 0.0159 | 3.45 | 0.0646 | 0.5054 | <.0001 | 0.4946 | <.0001 | N6224 | Immunoglobulin Kappa Light Chain Protein |
| 17 | N4411 | 0.0173 | 3.75 | 0.0543 | 0.4966 | <.0001 | 0.5034 | <.0001 | N4411 | Complement Factor H/Hs Protein |
| 18 | N6214 | 0.0147 | 3.17 | 0.0764 | 0.4893 | <.0001 | 0.5107 | <.0001 | N6214 | Fidgitin Protein II |
| 19 | N3417 | 0.0115 | 2.46 | 0.1186 | 0.4837 | <.0001 | 0.5163 | <.0001 | N3417 | Albumin Protein PRO2675 Protein |
| 20 | N4130 | 0.0149 | 3.17 | 0.0766 | 0.4765 | <.0001 | 0.5235 | <.0001 | N4130 | X2 Protein |
| 21 | N4402 | 0.0134 | 2.83 | 0.0937 | 0.4701 | <.0001 | 0.5299 | <.0001 | N4402 | Haptoglobin Related Protein |

Of the PD patients for which symptom severity was measured, 15 of 15 patients with mild PD (Hoehn and Yahr scale=1-2; UPDRS=13.7±4.9 SD), scored as PD (sensitivity 100%, see Table 8), and 28 of 31 patients with moderate to severe PD (Hoehn and Yahr scale=2.5-5; UPDRS=26.6±9.1 SD) scored as PD (sensitivity 90.3%, see Table 8).

TABLE 8

Probability of PD Diagnosis vs. Disease Severity
Sensitivity and Specificity of diagnosis by Linear Discriminant Analysis with 21 Biomarkers

| From Diagnosis | Classified Into Diagnosis | | Sensitivity | Specificity | Severity of PD Symptoms Hoehn & Yahr Scale* |
|---|---|---|---|---|---|
| | PD | Control | | | |
| PD | 15 | 0 | 100% | | Mild (HY 1-2) |
| PD | 28 | 3 | 90.3% | | Moderate-Severe HY (2.5-5) |
| PD | 43 | 3 | 93.5 | | Total PD (HY 1-5) |
| Control | 2 | 28 | | 93.3% | Control |

*HY 1-2: UPDRS 13.7 ± 4.89; HY 2.5-5: UPDRS 26.6 ± 9.07; (Avg. ± SD)
¥All patients under treatment with levodopa or other dopamine agonists
†Sensitivity and specificity by Receiver Operator Characteristics (ROC) of posterior probability of membership in diagnosis: >0.3707 = PD.

Figure 2A:
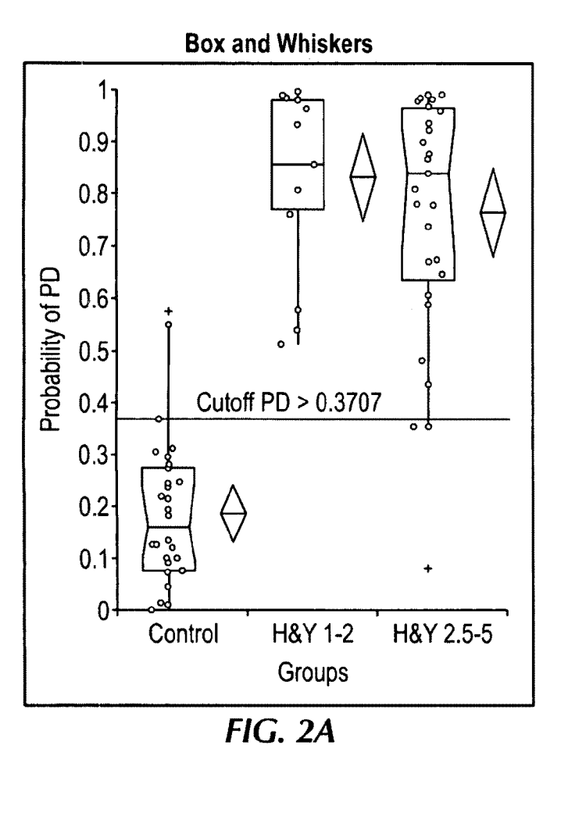
FIGS. 2A and 2B show a Box and Whiskers, Receiver Operator Characteristics and multivariate linear discriminant biostatistical analysis.
Figure 2B:
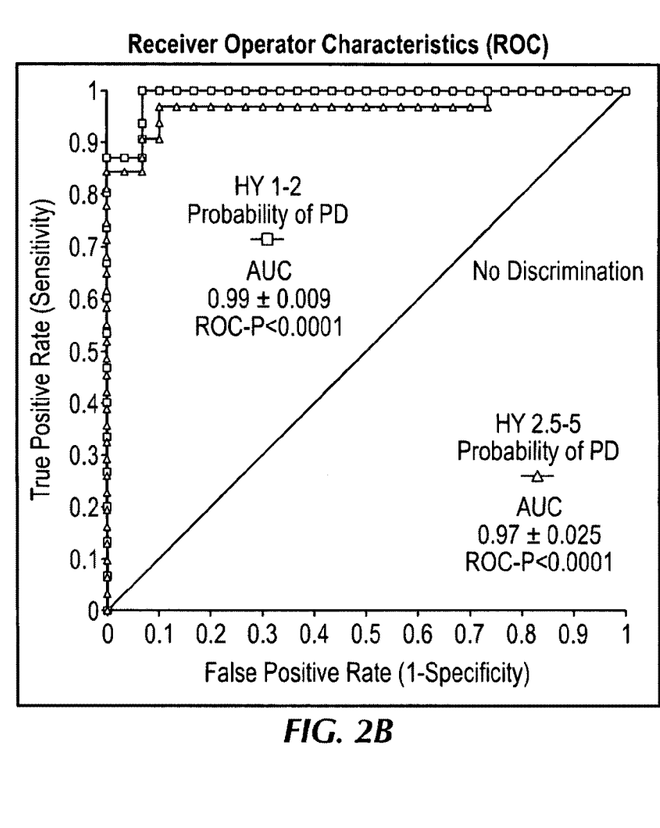
Figure 3:
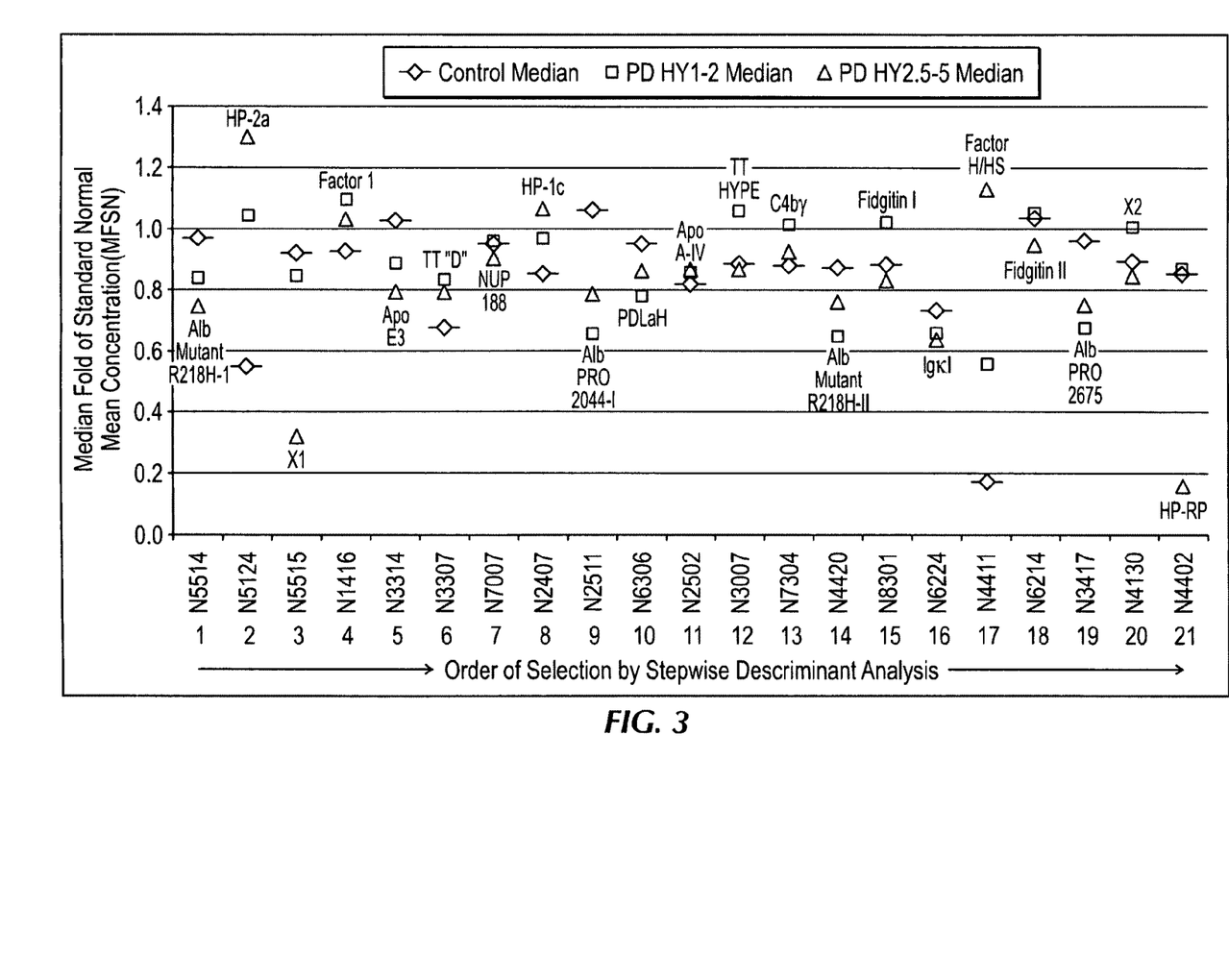
FIG. 3 illustrates the individual statistically significant abnormal concentrations in the 21 selected biomarkers in patients with mild and moderate-severe PD symptoms.

When the posterior probabilities of Parkinson's disease (PD-P) from discriminant analysis were compared by Dot, Box, and Whiskers graphs (FIG. 2A), and Receiver Operator Characteristics (ROC) plots (FIG. 2B), both PD groups showed marked separation from the controls (FIGS. 2, 3). Of the 21 selected proteins, 11 showed individual statistically significant abnormal concentrations in the patients with mild, and 14 with moderate-severe PD symptoms (FIG. 3, Table 9). Use of the concentrations of all 59 of the biomarkers in linear discriminant analysis provided a modest increase in sensitivity for PD diagnosis beyond using the 21 biomarker set (Table 5: A, 96.4% vs. B, 92.9%).

These results demonstrate that rigorous 2D gel technology coupled with image analysis can identify a collection of 59 serum proteins that were abnormally expressed in neurodegenerative diseases when compared to controls in banked, retrospectively analyzed samples. A novel investigation of these 59 biomarkers using a novel statistical approach has found that 21 of the protein biomarkers optimally classified PD and normal samples in prospectively collected samples when a multivariate discriminant analysis was applied to this set. When the same discriminant function was applied to the 2D gel data from a small test set of PD samples from an independent site that were not used for the determination of the function, it correctly identified all 6 of them.

The identities of these 21 protein biomarkers are consistent with mechanisms related to neuronal degeneration that are understood to be active in PD (FIG. 3, Table 2). The 36 remaining proteins of the 57 protein group still displayed substantial, statistically significant abnormal concentrations in PD patient sera. Like the 21 proteins, the 36 proteins are represented in the same four functional groups, and so add to the understanding of PD mechanisms. For some proteins, only specific isoforms or variants were among the 21, whereas the others were among the 36 not selected, for instance Apolipoprotein E3 was selected in the 21 biomarkers, while Apolipoprotein E4 was not selected; Haptoglobin HP-1c was selected, while Haptoglobin HP-1a, b, d, and e, were not selected; Immunoglobulin κd was selected, while Immunoglobulin κc was not selected; and Albumin PRO20444 was selected, while Albumin PRO2044-II not selected.

REFERENCES

All patents and publications mentioned in this specification are indicative of the level of skill of those of knowledge in the art to which the invention pertains. All patents and publications referred to in this application are incorporated herein by reference to the same extent as if each was specifically indicated as being incorporated by reference and to the extent that they provide materials and methods not specifically shown.

TABLE 9

Receiver Operator Characteristics of Fold of Standard Mean Concentration Values per Patients vs. Severity of PD Symptoms

| | Mild = HY 1-2 | | | | Moderate to Severe = HY 2.5-5 | | | |
|---|---|---|---|---|---|---|---|---|
| Biomarkers | HY 1-2 >/< Ctrl | AUC | SE | ROC-P | HY 2.5-5 >/< Ctrl | AUC | SE | ROC-P |
| N5514 | <Ctrl | 0.70 | 0.049 | <0.0001 | <Ctrl | 0.68 | 0.042 | <0.0001 |
| N5123 | >Ctrl | 0.68 | 0.052 | <0.0004 | >Ctrl | 0.74 | 0.039 | <0.0001 |
| N5515 | | | | | <Ctrl | 0.65 | 0.046 | <0.0007 |
| N1416 | >Ctrl | 0.63 | 0.054 | <0.010 | >Ctrl | 0.58 | 0.056 | <0.040 |
| N3314 | <Ctrl | 0.64 | 0.055 | <0.0050 | <Ctrl | 0.66 | 0.043 | <0.0002 |
| N2407 | >Ctrl | 0.67 | 0.042 | <0.0090 | >Ctrl | 0.63 | 0.055 | <0.0001 |
| N2511 | <Ctrl | 0.66 | 0.057 | <0.004 | <Ctrl | 0.65 | 0.044 | <0.0003 |
| N6306 | <Ctrl | 0.62 | 0.058 | <0.03 | <Ctrl | 0.60 | 0.044 | <0.010 |
| N3007 | >Ctrl | 0.64 ± 0.056 | | <0.0080 | | | | |
| N4420 | <Ctrl | 0.65 | 0.057 | <0.005 | | | | |
| N8301 | | | | | <Ctrl | 0.60 | 0.045 | <0.014 |
| N6224 | <Ctrl | 0.62 | 0.054 | <0.02 | <Ctrl | 0.60 | 0.045 | <0.020 |
| N4411 | | | | | >Ctrl | 0.62 | 0.044 | <0.003 |
| N3417 | <Ctrl | 0.68 | 0.054 | <0.0006 | <Ctrl | 0.66 | 0.043 | <0.0001 |
| N4130 | | | | | <Ctrl | 0.58 | 0.045 | <0.050 |
| N4402 | | | | | <Ctrl | 0.63 | 0.044 | <0.002 |
| The 21 Combined‡ | PD-P > 0.3701 | 0.99 | 0.009 | <0.0001 | PD-P > 0.3701 | 0.97 | 0.025 | <0.0001 |

1. D. A. Bennett, L. A. Beckett, A. M. Murray, et al., Prevalence of parkinsonian signs and associated mortality in a community population of older people, N. Engl. J. Med. 334 (1996) 71-76.
2. M. M. Hoehn, M. D., Yahr, Parkinsonism: onset, progression, and mortality, Neurology 17 (1967) 427-42.
3. J. Jankovic, A. H. Rajput, M. P. McDermott, D. P. Perl, Parkinson Study Group, The evolution of diagnosis in early Parkinson disease, Arch. Neurol. 57 (2000) 369-72.
4. A. Schrag, Y. Ben-Shlomo, N. Quinn, How valid is the clinical diagnosis of Parkinson's disease in the community? J. Neurol. Neurosurg. Psychiatry 73 (2002) 529-34.
5. E. Tolosa, G. Wenning, W. Poewe, The diagnosis of Parkinson's disease, Lancet Neurol. 5 (2006) 75-86.
6. M. H. Polymeropoulos, C. Lavedan, E. Leroy, et al., Mutation in the alpha-synuclein gene identified in families with Parkinson's disease. Science. 276 (1997) 2045-7.
7. K. Markopoulou, J. W. Langston, Candidate genes and Parkinson's disease: where to next? Neurology 53 (1999) 1382-3.
8. R. Krüger, W. Kuhn, T. Müller, et al., Ala30Pro mutation in the gene encoding alpha-synuclein in Parkinson's disease, Nat. Genet. 18 (1998) 106-8.
9. J. Margolis, K. J. Kendrick, 2-dimensional resolution of plasma proteins by combination of polyacrylamide disc and gradient gel electrophoresis, Nature 221 (1969) 1056-1057.
10. L. R. Orrick, M. O. J. Olson, H. Busch, Comparison of nucleolar proteins of normal rat liver and Novikoff hepatoma ascites cells by two-dimensional polyacrylamide gel electrophoresis, Proc. Nat. Acad. Sci. USA 70 (1973) 1316-1320.
11. I. L. Goldknopf, C. W. Taylor, R. M. Baum, L. C. Yeoman, M. O. J. Olson, A. W. Prestayko, H. Busch, Isolation and characterization of protein A24, a "histone-like" nonhistone chromosomal protein, J. Biol. Chem. 250, (1975) 7182-7187.
12. I. L. Goldknopf, H. Busch, Remarkable similarities of peptide fingerprints of histone 2A and nonhistone chromosomal protein A24, Biochem. Biophys. Res. Commun. 65, (1975) 951-960.
13. Olson M. O. J., Goldknopf I. L., K. A. Guetzow, G. T. James, T. C. Hawkins, C. J. Mays-Rothberg, H. Busch, The NH2- and COOH-terminal amino acid sequence of nuclear protein A24, J. Biol. Chem. 251, (1976) 5901-5903.
14. I. L. Goldknopf, H. Busch, Isopeptide linkage between nonhistone and histone 2A polypeptides of chromosomal conjugate-protein A24, Proc. Nat. Acad. Sci. USA 74, (1977) 864-868.
15. I. L. Goldknopf, M. F. French, R. Musso, H. Busch, Presence of protein A24 in rat liver nucleosomes, Proc. Nat. Acad. Sci. USA 74, (1977) 5492-5495.
16. L. Anderson, N. G. Anderson, High resolution two-dimensional electrophoresis of human plasma proteins, Proc. Nat. Acad. Sci. USA 74, (1977) 5421-5425.
17. J. Klose, Protein mapping by combined isoelectric focusing and electrophoresis of mouse tissues. A novel approach to testing for induced point mutations in mammals, Humangenetik. 26, (1975) 231-243.
18. P. H. O'Farrell, High resolution two-dimensional electrophoresis of proteins, J. Biol. Chem. 250, (1975) 4007-4021.
19. H. M. Kuerer, I. L. Goldknopf, H. Fritsche, S. Krishnamurthy, E. A. Sheta, K. Hunt, Identification of distinct protein expression patterns in bilateral matched pair breast ductal fluid specimens from women with unilateral invasive breast carcinoma. Cancer 95, (2002) 2276-2282.
20. T. Kuncewicz, E. A. Sheta, I. L. Goldknopf, B. C. Kone, Proteomic analysis of S-nitrosylated proteins in mesangial cells. Mol. Cell. Proteomics 2, (2003) 156-163.
21. D. Peng, D. A. Sheta, S. M. Powell, C. A. Moskaluk, K. Washington, I. L. Goldknopf, W. El-Rifai, Alterations in Barrett's-related adenocarcinomas: A proteomic approach. Int. J. Cancer 122, (2008) 1303-1310.
22. I. L. Goldknopf, E. A. Sheta, J. Bryson, B. Folsom, C. Wilson, J. Duty, A. A. Yen, S. H. Appel, Complement C3c and related protein biomarkers in amyotrophic lateral sclerosis and Parkinson's disease. Biochemical and Biophysical Research Communications 342 (2006) 1034-1039.
23. I. L. Goldknopf, Molecular diagnostics and proteomics on the outskirts of personalized medicine, Joint Meeting of the Molecular Diagnostics and Cancer Proteomics World Congresses, Expert Rev. Mol. Diagnostics. 7, (2007) 339-343.
24. I. L. Goldknopf, Blood-based proteomics for personalized medicine: examples from neurodegenerative disease. Expert Rev. Proteomics 5, 1-8 (2008).
25. E. A. Sheta, S. H. Appel, I L. Goldknopf, 2D gel blood serum protein biomarkers reveal differential clinical proteomics of the neurodegenerative diseases. Expert Rev. Proteomics 3(1), (2006) 45-62.
26. S. Fahn, R. Elton, Members of the UPDRS Development Committee. In: S. Fahn, C. D. Marsden, D. B. Calne, M. Goldstein, eds, Recent Developments in Parkinson's *Disease, Vol.* 2 Florham Park, N. J., Macmillan Health Care Information (1987), pp 153-163, 293-304.
27. H. Braak, R. A. de Vos, J. Bohl, K. Del Tredici, Gastric alpha-synuclein immunoreactive inclusions in Meissner's and Auerbach's plexuses in cases staged for Parkinson's disease-related brain pathology, Neurosci. Lett. 396, (2006) 67-72.
28. H. Bernheimer, W. Birkmayer, O. Hornykiewicz, et al., Brain dopamine and the syndromes of Parkinson and Huntington. Clinical, morphological and neurochemical correlations, J. Neurol. Sci. 20 (1973) 415-55.
29. A. E. Lang, A. M. Lozano, Parkinson's disease, Review, First and Second of two parts, N. Engl. J. Med. 339, (1998) 1130-53.
30. E. C. Wolters, H. Braak, Parkinson's disease: premotor clinico-pathological correlations, J. Neural. Transm. Suppl. 70 (2006) 309-19.
31. E. Bezard, C. E. Gross, Compensatory mechanisms in experimental and human parkinsonism: towards a dynamic approach, Prog. Neurobiol. 55 (1998) 93-116.
32. E. Bezard, A. R. Crossman, C. E. Gross, J. M. Brotchie, Structures outside the basal ganglia may compensate for dopamine loss in the presymptomatic stages of Parkinson's disease, FASEB J. 15 (2001) 1092-4.
33. M. Rodriguez, E. Pereda, J. González, et al., How is firing activity of substantia nigra cells regulated? Relevance of pattern-code in the basal ganglia, Synapse. 49 (2003) 216-25.
34. Y. Baba, A. Kuroiwa, R. J. Uitti, et al., Alterations of T-lymphocyte populations in Parkinson disease. Parkinsonism Relat. Disord. 11 (2005) 493-8.
35. J. W. Langston, The Parkinson's complex: parkinsonism is just the tip of the iceberg. Ann. Neurol. 59 (2006) 591-6.

36. J. J. Zarranz, J. Alegre, J. C. Gómez-Esteban, et al., The new mutation, E46K, of alpha-synuclein causes Parkinson and Lewy body dementia. Ann. Neurol. 55 (2004) 164-73.
37. T. Kitada, S. Asakawa, N. Hattori, et al., Mutations in the parkin gene cause autosomal recessive juvenile parkinsonism. Nature. 392 (1998) 605-8.
38. K. Hedrich, C. Eskelson, B. Wilmot, et al., Distribution, type, and origin of Parkin mutations: review and case studies, Mov. Disord. 19 (2004) 1146-57.
39. E. Leroy, R. Boyer, G. Auburger, et al., The ubiquitin pathway in Parkinson's disease, Nature 395 (1998) 451-2.
40. V. Bonifati, P. Rizzu, F. Squitieri, et al., DJ-1(PARK7), a novel gene for autosomal recessive, early onset parkinsonism, Neurol. Sci. 24 (2003) 159-60.
41. E. M. Valente, P. M. Abou-Sleiman, V. Caputo, et al., Hereditary early-onset Parkinson's disease caused by mutations in PINK1. Science. 304 (2004) 1158-60.
42. C. Paisán-Ruíz, S. Jain, E. W. Evans, et al., Cloning of the gene containing mutations that cause PARK8-linked Parkinson's disease, Neuron. 44 (2004) 575-7.
[43] A. Zimprich, S. Biskup, P. Leitner, et al., Mutations in LRRK2 cause autosomal-dominant parkinsonism with pleomorphic pathology, Neuron. 44 (2004) 601-7.
44. R. Krüger, LRRK2 in Parkinson's disease—drawing the curtain of penetrance: a commentary. BMC Med. 6 (2008) 33.
45. O. A. Ross, A. I. Soto, C. Vilariño-Güell, et al., Genetic variation of Omi/HtrA2 and Parkinson's disease, Parkinsonism Relat. Disord. 14 (2008) 539-43.
46. A. Di Fonzo, M. C. Dekker, P. Montagna, et al., FBXO7 mutations cause autosomal recessive, early-onset parkinsonian-pyramidal syndrome, Neurology. 72 (2009) 240-5.
47. M. G. Spillantini, M. L. Schmidt, V. M. Lee, J. Q. Trojanowski, R. Jakes, M. Goedert, Alpha-synuclein in Lewy bodies, Nature 388 (1997) 839-40.
48. D. Campion, C. Martin, R. Heilig, et al., The NACP/synuclein gene: chromosomal assignment and screening for alterations in Alzheimer disease, Genomics 26 (1995) 254-7.
49. J. Q. Trojanowski, V. M. Lee, Parkinson's disease and related synucleinopathies are a new class of nervous system amyloidoses, Neurotoxicology 23 (2002) 457-60.
50. J. T. Greenamyre, T. G. Hastings, Biomedicine. Parkinson's—divergent causes, convergent mechanisms, Science. 304 (2004) 1120-2.
51. K. Uéda, T. Saitoh, H. Mori, Tissue-dependent alternative splicing of mRNA for NACP, the precursor of non-A beta component of Alzheimer's disease amyloid. Biochem. Biophys. Res. Commun. 205 (1994) 1366-72.
52. E. R. Dorsey, R. G. Holloway, B. M. Ravina, Biomarkers in Parkinson's disease, Expert Rev. Neurother. 6 (2006) 823-31.
53. A. W. Michell, S. J. Lewis, T. Foltynie, R. A. Barker, Biomarkers and Parkinson's disease, Brain 127 (2004) 1693-705.
54. F. Borovecki, L. Lovrecic, J. Zhou, et al., Genome-wide expression profiling of human blood reveals biomarkers for Huntington's disease, Proc. Natl. Acad. Sci. USA 102 (2005) 11023-8.
55. L. Emilsson, P. Saetre, E. Jazin, Alzheimer's disease: mRNA expression profiles of multiple patients show alterations of genes involved with calcium signaling, Neurobiol. Dis. 21 (2006) 618-25.
56. O. C. Maes, S. Xu, B. Yu, et al., Transcriptional profiling of Alzheimer blood mononuclear cells by microarray, Neurobiol. Aging 28 (2007) 1795-809.
57. C. E. Teunissen, D. Lütjohann, K. von Bergmann, et al., Combination of serum markers related to several mechanisms in Alzheimer's disease. Neurobiol. Aging 24 (2003) 893-902.
58. R. Ricciarelli, C. d'Abramo, S. Massone, et al., Microarray analysis in Alzheimer's disease and normal aging, IUBMB Life 56 (2004) 349-54.
59. E. M. Blalock, J. W. Geddes, K. C. Chen, et al., Incipient Alzheimer's disease: microarray correlation analyses reveal major transcriptional and tumor suppressor responses, Proc. Natl. Acad. Sci. USA. 101 (2004) 2173-8.
60. J. Kálman, K. Kitajka, M. Páláski, et al., Gene expression profile analysis of lymphocytes from Alzheimer's patients, Psychiatr. Genet. 15 (2005) 1-6.
61. M. F. Lopez, A. Mikulskis, S. Kuzdzal, et al., High-resolution serum proteomic profiling of Alzheimer disease samples reveals disease-specific, carrier-protein-bound mass signatures, Clin. Chem. 51 (2005) 1946-54.
62. F. Abdi, J. F. Quinn, J. Jankovic, et al., Detection of biomarkers with a multiplex quantitative proteomic platform in cerebrospinal fluid of patients with neurodegenerative disorders, J. Alzheimer's Dis. 9 (2006) 293-348.
63. F. Blandini, E. Sinforiani, C. Pacchetti, et al., Peripheral proteasome and caspase activity in Parkinson disease and Alzheimer disease, Neurology 66 (2006) 529-34.
64. F. Blandini, M. Cosentino, A. Mangiagalli, et al., Modifications of apoptosis-related protein levels in lymphocytes of patients with Parkinson's disease. The effect of dopaminergic treatment, J. Neural. Transm. 111 (2004) 1017-30.

What is claimed is:

1. A method comprising:
   analyzing a serum sample from a test subject for a change in expression of a set of protein biomarkers,
   wherein the set of protein biomarkers comprises Chain A Albumin mutant R218H protein and one or more biomarkers selected from the group consisting of Haptoglobin HP-2a protein, Complement Factor I protein, Apolipoprotein E3 protein, Transthyretin dimer protein, Nucleoporin NUP 188 protein, Haptoglobin HP-1 protein, Albumin protein PRQ2044, Parkinson's LB acidic H2A protein, Apolipoprotein A-IV protein, Transthyretin Huntington Interacting Protein E, Complement C4b gamma chain protein, Fidgitin I protein, Immunoglobulin kappa light chain protein, Complement Factor H/Hs protein, Fidgitin II protein, Albumin protein PRQ2675, Haptoglobin related protein, and any combination thereof.

2. The method of claim 1, wherein Chain A Albumin mutant R218H protein comprises Chain A Albumin mutant R218H I, Chain A Albumin mutant R218H II, or a combination thereof.

3. A method comprising:
   electrophoresing a portion of a serum sample from a test subject on a 2D gel, wherein the portion of the serum sample has a standardized protein concentration;
   measuring a pixel cell density for each of a set of protein biomarkers in the 2D gel; and
   comparing the pixel cell density of each of the set of protein biomarkers with a mean cell pixel density determined for a control serum,
   wherein the set of protein biomarkers comprises Chain A Albumin mutant R218H protein and one or more biomarkers selected from the group consisting of Haptoglobin HP-2a protein, Complement Factor I protein, Apolipoprotein E3 protein, Transthyretin dimer protein, Nucleoporin NUP 188 protein, Haptoglobin HP-1 protein, Albumin protein PRQ2044, Parkinson's LB acidic H2A protein, Apolipoprotein A-IV protein, Transthyretin Huntington Interacting Protein E, Complement C4b gamma chain protein, Fidgitin I protein, Immunoglobulin kappa light chain protein, Complement Factor H/Hs protein, Fidgitin II protein, Albumin protein PRQ2675, Haptoglobin related protein, or any combination thereof.

4. A method comprising:
(a) electrophoresing a portion of a serum sample from a subject on a 2D gel;
(b) measuring a protein spot density in the 2D gel for each of a set of protein biomarkers, wherein the set of protein biomarkers comprises Chain A Albumin Mutant R218H Protein, and one or more biomarkers selected from the group consisting of Haptoglobin HP-2a Protein, Complement Factor I Protein, Apolipoprotein E3 Protein, Haptoglobin HP-1 Protein, Albumin Protein PRO2044, PDLaH Parkinson's LB acidic H2A Protein (ADPR/ub/A24), Immunoglobulin Kappa Light Chain Protein, Albumin Protein PR02657, Transthyretin HYPE Protein, Fidgitin Protein I, Complement Factor H/Hs Protein, Haptoglobin related Protein, or any combination thereof; and
(c) comparing the protein spot densities for each of the set of protein biomarkers with standard control mean values.

5. The method of claim 4, further comprising staining the 2D gel prior to measuring the protein spot density for each of the set of protein biomarkers.

6. The method of claim 4, wherein the standard control mean values for each of the set of protein biomarkers are measured from one or more serum samples from a control population.

7. The method of claim 4, wherein the comparing comprises calculating a fold of standard normal mean concentration (FSM) for each of the set of protein biomarkers by dividing the protein spot densities by the standard control mean values.

8. The method of claim 4, wherein the method further comprises a linear discrimination analysis.

9. The method of claim 4, wherein the set of protein biomarkers further comprises Transthyretin dimer Protein, Nucleoporin NUP188, Apolipoprotein A-IV Protein, Complement C4b Gamma Chain Protein, Fidgitin Protein II, or a combination thereof.

10. The method of claim 4, wherein the set of protein biomarkers further comprises Apolipoprotein E4, Alpha-2-macroglobulin, Aldehyde dehydrogenase 1 A3, Apolipoprotein H, Pre-serum Amyloid P protein, AIM apoptosis Inhibitor (CD5 Scavenger Receptor), Glutathione S Transferase Mu5-5, Lectin 3 P35, Alpha-1-microglobulin, Clusterin Isoform 1, Preapolipoprotein E, Immunoglobulin kappa C region protein, Hemopexin, Complement Factor Bb protein, Complement C3c1a, Complement C3c1b, Complement C3c1c, Complement C3c2a, Complement C3c2b, Complement C3dg, Complement cytolysis inhibitor protein alpha subunit, Inter α trypsin inhibitor heavy chain H4 related 35KD protein, Albumin protein, Similar to Albumin protein, Transferrin protein, or a combination thereof.

11. The method of claim 9, wherein the set of protein biomarkers further comprises Apolipoprotein E4, Alpha-2-macroglobulin, Aldehyde dehydrogenase 1 A3, Apolipoprotein H, Pre-serum Amyloid P protein, AIM apoptosis Inhibitor (CD5 Scavenger Receptor), Glutathione S Transferase Mu5-5, Lectin 3 P35, Alpha-1-microglobulin, Clusterin Isoform 1, Preapolipoprotein E, Immunoglobulin kappa C region protein, Hemopexin, Complement Factor Bb protein, Complement C3c1a, Complement C3c1b, Complement C3c1c, Complement C3c2a, Complement C3c2b, Complement C3dg, Complement cytolysis inhibitor protein alpha subunit, Inter α trypsin inhibitor heavy chain H4 related 35KD protein, Albumin protein, Similar to Albumin protein, Transferrin protein, or a combination thereof.

12. The method of claim 4, wherein the set of protein biomarkers comprises Chain A Albumin mutant R218H I protein, Haptoglobin HP-2a protein, X1 Protein, Complement Factor I protein, Apolipoprotein E3 protein, Transthyretin dimer protein, Nucleoporin NUP 188 protein, Haptoglobin HP-1 protein, Albumin protein PRO2044, Parkinson's LB acidic H2A protein, Apolipoprotein A-IV protein, Transthyretin Huntington Interacting Protein E, Complement C4b gamma chain protein, Chain A Albumin mutant R218H II protein, Fidgitin I protein, Immunoglobulin kappa light chain protein, Complement Factor H/Hs protein, Fidgitin II protein, Albumin protein PRO2675, X2 protein, and Haptoglobin related protein.

13. The method of claim 4, wherein the portion of the serum sample comprises a standardized protein amount.

14. The method of claim 13, wherein the standardized protein amount is about 100 μg.

15. The method of claim 1, wherein the set of protein biomarkers comprises Chain A Albumin mutant R218H I protein, Haptoglobin HP-2a protein, Complement Factor I protein, Apolipoprotein E3 protein, Transthyretin dimer protein, Nucleoporin NUP 188 protein, Haptoglobin HP-1 protein, Albumin protein PRO2044, Parkinson's LB acidic H2A protein, Apolipoprotein A-IV protein, Transthyretin Huntington Interacting Protein E, Complement C4b gamma chain protein, Chain A Albumin mutant R218H II protein, Fidgitin I protein, Immunoglobulin kappa light chain protein, Complement Factor H/Hs protein, Fidgitin II protein, Albumin protein PRO2675, and Haptoglobin related protein.

16. The method of claim 3, wherein the set of protein biomarkers comprises Chain A Albumin mutant R218H I protein, Haptoglobin HP-2a protein, Complement Factor I protein, Apolipoprotein E3 protein, Transthyretin dimer protein, Nucleoporin NUP 188 protein, Haptoglobin HP-1 protein, Albumin protein PRO2044, Parkinson's LB acidic H2A protein, Apolipoprotein A-IV protein, Transthyretin Huntington Interacting Protein E, Complement C4b gamma chain protein, Chain A Albumin mutant R218H II protein, Fidgitin I protein, Immunoglobulin kappa light chain protein, Complement Factor H/Hs protein, Fidgitin II protein, Albumin protein PRO2675, and Haptoglobin related protein.

\* \* \* \* \*